United States Patent [19]

Garst et al.

[11] Patent Number: 4,725,620
[45] Date of Patent: Feb. 16, 1988

[54] 2H-PYRAN-2,6-(3H)-DIONE DERIVATIVES WITH ANTI-ALLERGIC ACTIVITY

[75] Inventors: Michael E. Garst, Newport Beach; Charles Gluchowski, Mission Viejo; Lester J. Kaplan, Irvine, all of Calif.

[73] Assignee: Allergan, Inc., Irvine, Calif.

[21] Appl. No.: 905,822

[22] Filed: Sep. 10, 1986

[51] Int. Cl.⁴ .................... A61K 31/35; C07D 309/36
[52] U.S. Cl. ........................................ 514/460; 549/231
[58] Field of Search ........................ 549/231; 514/460

[56] References Cited

U.S. PATENT DOCUMENTS 4,165,365 8/1979 Snader ............................ 549/231 X

OTHER PUBLICATIONS

Snader et al., J. Med. Chem., vol. 22, No. 6 (1979) pp. 1-158, 706-174.
Cramer et al., Journal of Medicinal Chemistry, vol. 22, No. 6 (1979) pp. 714-724.

Primary Examiner—Richard L. Raymond
Attorney, Agent, or Firm—James Kanagy

[57] ABSTRACT

Achiral compounds of a 2H-pyran-2,6(3H)-dione derivative of the formula

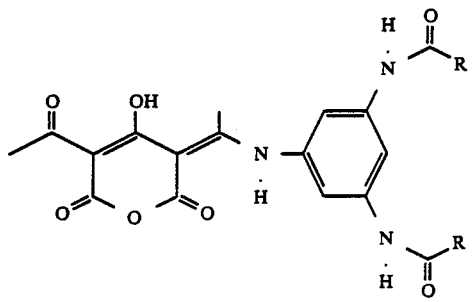

or a pharmaceutically acceptable salt thereof, where R is $-(CH_2)_mOH$ or $-CH((CH_2)_nCH_2OH)_2$ where m is 1-5 and n is 0-4. These compounds are useful in the treatment of allergic conditions.

7 Claims, No Drawings

2H-PYRAN-2,6-(3H)-DIONE DERIVATIVES WITH ANTI-ALLERGIC ACTIVITY

BACKGROUND

This invention relates to substituted achiral 2H-pyran-2,6-(3H)-dione derivatives which are useful for inhibiting the symptoms of an allergic response resulting for an antigen-antibody reaction. More specifically, the compounds of this invention are surprisingly effective in inhibiting the release and/or formation and release of pharmacologically active mediators such as histamine, serotonin and slow-reacting substance of anaphylaxis (SRS-A) from effector cells which are produced and/or released as a result of an interaction of antigen and specific antibody fixed to the cell surface (allergic reaction). These properties enable the subject compounds to be useful in various allergic diseases such as allergic ocular diseases, asthma, rhinitis and urticaria.

The compounds of this invention are represented by the following general structural formula:

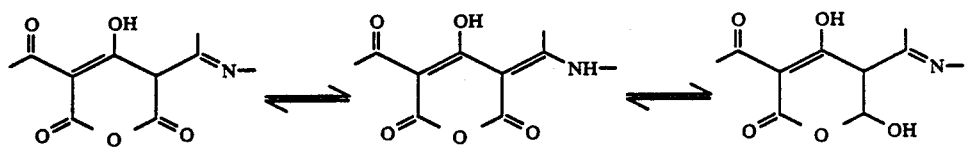

or a pharmaceutically acceptable salt thereof, where R is $-(CH_2)_m OH$ or $-CH((CH_2)_n CH_2OH)_2$ where m is 1-5 and n is 1-4.

These compounds are conveniently prepared, as a last step reaction, as follows.

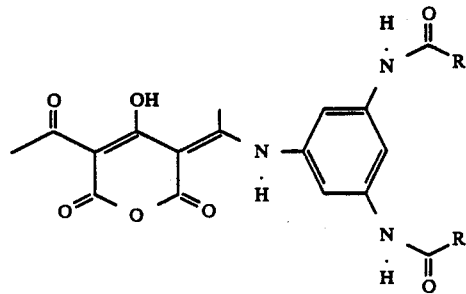

Thus, the 3,5-diacetyl-4,6-dihydroxy-2H-pyran-2-one and the appropriately substituted aniline are heated at reflux in an appropriate organic solvent, an alcohol such as methanol for example, for one to three hours to give the product.

Mono- and di-alkyl metal salts, such as the mono- and di-sodium or potassium salts are readily obtained by treatment with the appropriate alkali metal alkoxide, for example methoxide, in an alkanol solvent such as methanol. They can also be prepared by treatment with aqueous alkali metal hydroxides in water.

The pyran-2-one starting material is obtained by reaction of acetonedicarboxylic acid with acetic anhydride in sulfuric acid at elevated temperature. The reaction product actually has several tautomeric structures as shown in U.S. Pat. No. 4,165,365 but for convenience it is designated here as 3,5-diacetyl-4,6-dihydroxy-2H-pyran-2-one. Due to the tautomeric forms of the pyran-2-one starting material, these compounds will have the following tautomeric structures:

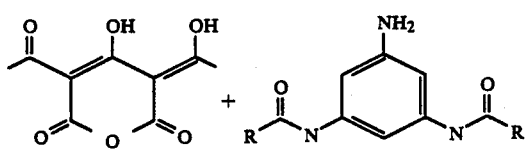

where Ar is an aniline fragment of the same structure as represented by formula I. Convenience dictates use of one tautomeric form. The enamine pyran-2,6-dione form has been chosen to represent all tautomeric forms here. It is fully intended that all tautomeric forms are covered by this invention. The use of this single tautomer to represent the invention is not limiting of the invention.

The substituted aniline starting materials used herein are conveniently prepared by established preparative methods.

Wiley, R. H., et. al., *J. Org. Chem.*, 21, 686–688 (1956) has reported the reaction of amines with reaction product of acetonedicarboxylic acid and acetic anhydride, the latter designated 5-carboxydehydroacetic acid. Similarly, Kiang, A. K. et. al. *J. Chem. Soc.*, 2721-6, (1971) has disclosed such reaction products with amines. However, there is no disclosure of products represented by formula I. See also U.S. Pat. No. 4,165,365, issued Aug. 21, 1979 for a similar method for preparing substituted anilines.

The substituted aniline structures of this invention were prepared by the following schematics. The symbol R refers to a protecting group in each of these schemes. Compounds where R is $-CH_2OH$ are prepared as follows:

Reaction Scheme I

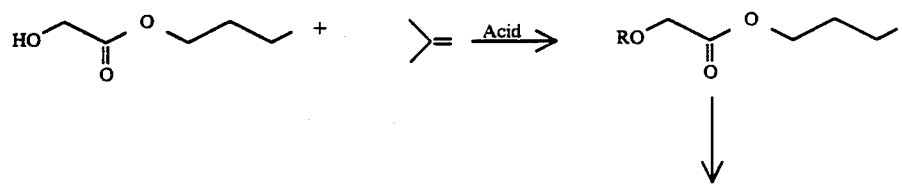

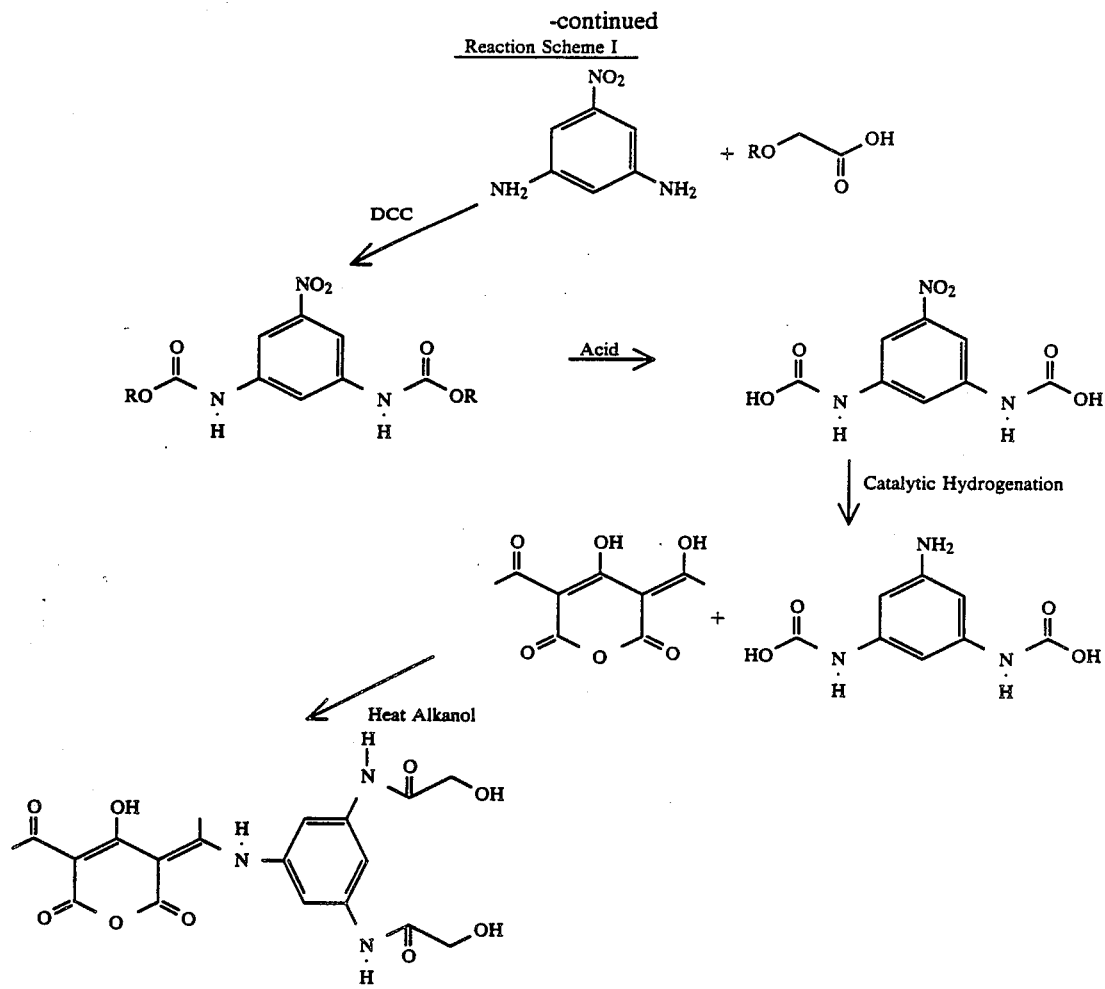
Compounds where R is —CH(CH$_2$OH)$_2$, are prepared as illustrated in Reaction Scheme II.
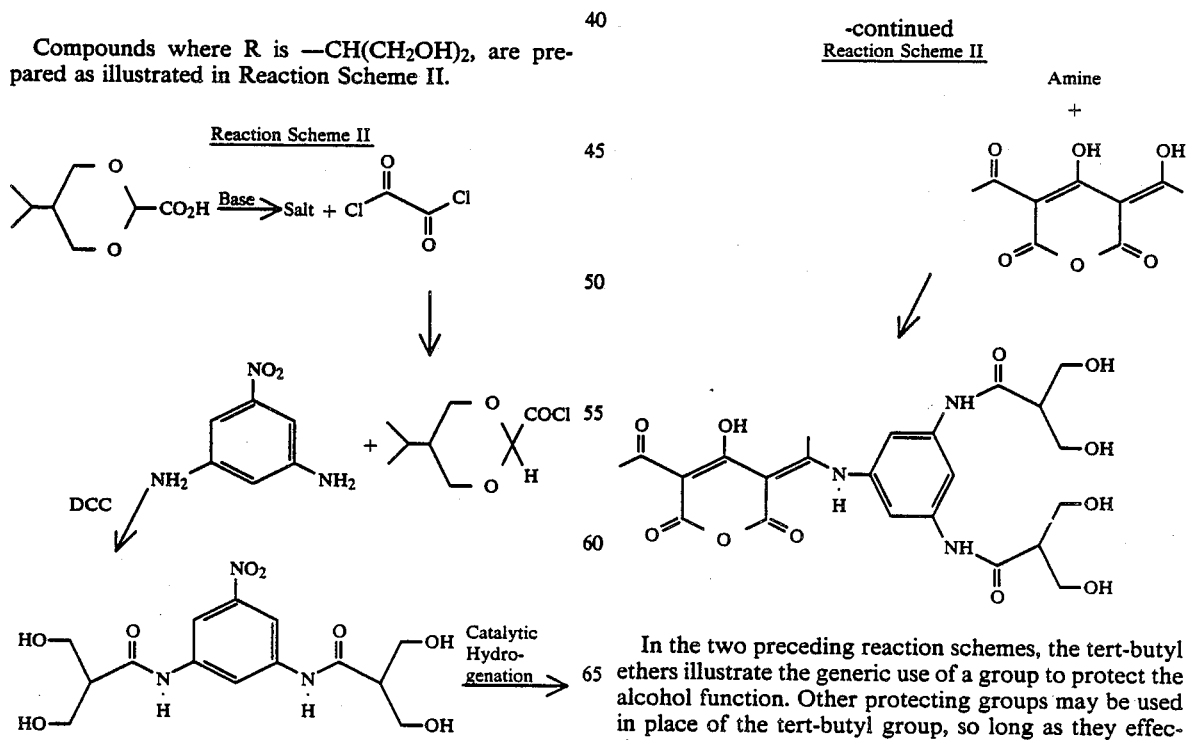
In the two preceding reaction schemes, the tert-butyl ethers illustrate the generic use of a group to protect the alcohol function. Other protecting groups may be used in place of the tert-butyl group, so long as they effectively protect the particular alcohol.

The hydroxy acids needed to make substituted anilines where R equals —(CH$_2$)$_m$OH and m is 2-5 are prepared as illustrated in reaction Scheme III. These acids are then used in place of formula 4 in Reaction Scheme I to form substituted anilines which are used to make compounds of formula I as illustrated in the remaining steps of Reaction Scheme I.

Reaction Scheme III

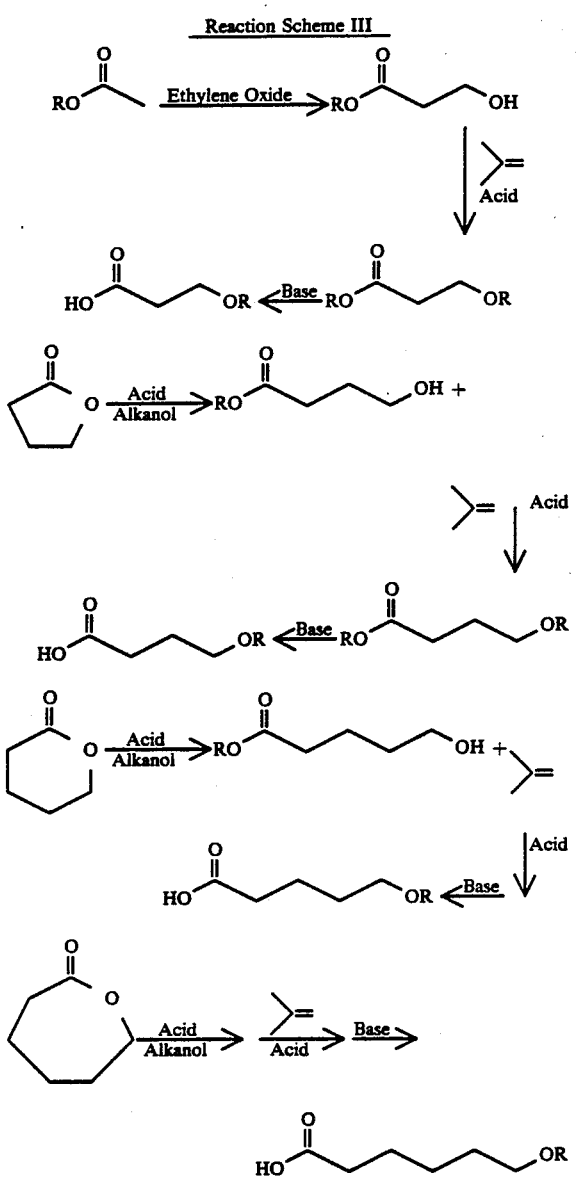

Where m is 2, the ester of acetic acid is deprotonated with a strong base and alkylated with ethylene oxide to obtain the 3-hydroxypropionate (M. Rathke et. al., *J. Am. Chem. Soc.*, 1971, 93, 2319). Herein, it is preferred to use the tert-butyl acetate and lithium diisopropylamide (LDA) as the base in the presence of ethylene oxide to yield tert-butyl-3-hydroxypropionate.

The free hydroxyl group can be protected by conversion to an ether, preferably the tert-butyl ether effected by treating the 3-hydroxypropionate with isobutylene in the presence of an acid such as sulfuric acid.

The free acid can be prepared by basic hydrolysis, preferably in the presence of sodium carborate in water and methanol. This acid (3-tert-butoxypropionic acid) can be converted to the substituted aniline (m=2) as illustrated in Examples 3, 4 and 5.

For m is 3, gamma-butyrolactone can be converted to 4-tert-butoxybutyric acid by ring opening in the presence of an alkanol such as methanol and a catalytic amount of a mineral acid such as sulfuric acid (S. Patai, "The Chemistry of Carboxylic Acids and Esters", pp. 103-136; Interscience Publishers, New York, 1969); protection of the free hydroxyl as an ether, preferably as the tert-butyl ether; and basic hydrolysis using the conditions described above. This protected 4-hydroxybutyric acid can be converted to the substituted aniline (m=3) as illustrated in Examples 3, 4 and 5.

Where m is 4, delta-valerolactone can be converted to protected 5-hydroxypentanoic acid (example: 5-tert-butoxypentanoic acid) as described for 4-hydroxybutyric acid in the preceding paragraph. This acid can be converted to the substituted aniline (m=4) as illustrated in Examples 3, 4 and 5.

2-Oxepanone can be converted to a protected 6-hydroxyhexanoic acid as described for the 4-hydroxybutyric acid. These acids can be converted to the substituted aniline (m=5) as illustrated in Examples 3, 4 and 5.

Substituted anilines where R is —CH((CH$_2$)nOH)$_2$ and n is 2-4 are prepared as illustrated in Reaction Scheme IV.

Reaction Scheme IV

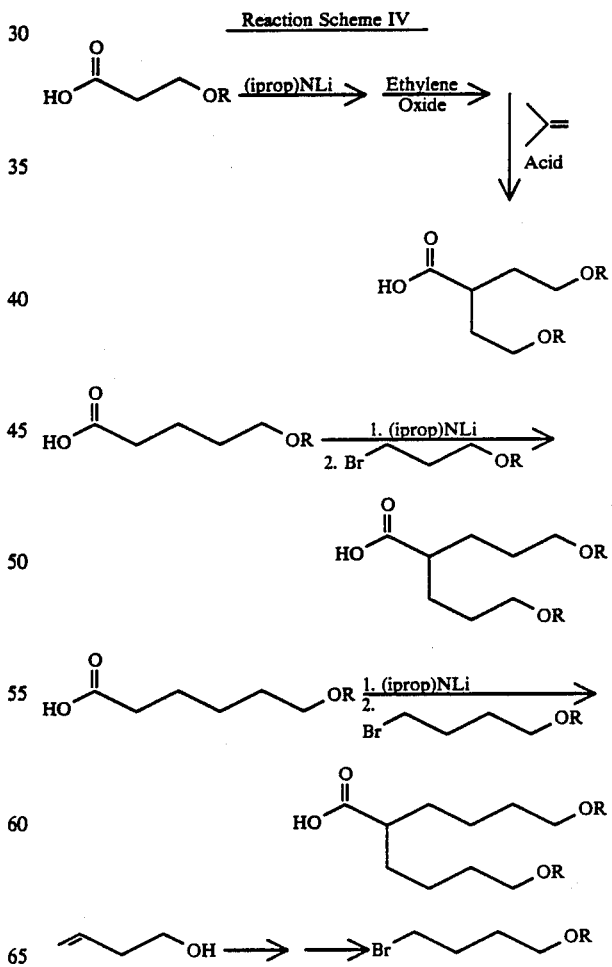

Thus, for n equals 2, a protected 3-hydroxypropionic acid (eg., 3-tert-butoxypropionic acid) can be deprotonated with a strong base such as LDA and alkylated with ethylene oxide. This intermediate alcohol can be protected as an ether, preferably as the tert-butyl ether in the presence of isobutylene and sulfuric acid to yield a compound illustrated by 2-(2-tert-butoxyethyl)-4-tert-butyoxybuturic acid. This acid can be converted to the aniline (n=2) as illustrated in Examples 3, 4 and 5.

For n equals 3, 4-alkoxybutyric acid can be deprotonated with a strong base such as LDA and alkylated with 1-bromo-3-(tert-butoxy)propane (prepared by protection of 3-bromopropanol). This yields 53(3-tert-butoxypropyl)-5-tert-butoxypentanoic acid which can be converted to the aniline (n=3) as illustrated in examples 3, 4 and 5.

Where n is 4, 5-alkoxypentanoic acid, or a similarly protected 5-hydroxypentanoic acid, can be deprotonated with a strong base such as LDA and alkylated with 1-bromo-4-tert-butoxybutane (prepared from 3-butene-1-ol by bromination to the terminus of the double bond and protection of the hydroxyl group). This yields a 2-(4-tert-butoxybutyl)-6-tert-butoxyhexanoic acid, or similarly protected compound, which can be converted to the aniline (n=4) as illustrated in Examples 3, 4 and 5.

The preferred compounds are those where R is —$(CH_2)_mOH$ and —$CH((CH_2)_nCH_2OH)_2$ and where m is 1–5 and 0–4. Most preferred are:

5-acetyl-4-hydroxy-3-[1-[[3,5-bis-N-(2-hydroxymethyl-3-hydroxy-propionamido)phenyl]amino]ethylidene]-2H-pyran-2,6-(3H)-dione; and 5-acetyl-4-hydroxy-3-[1-[[3,5-bis-N-(2-hydroxymethyl-3-hydroxy-propionamido)phenyl]amino]ethylidene]-2H-pyran-2,6-(3H)-dione.

Included in this invention is the method of inhibiting the symptoms of an allergic response resulting from an antigen-antibody reaction which comprises administering to an animal a therapeutically effective amount for producing said inhibition of a compound of formula I, preferably in the form of a pharmaceutical composition. The administration may be carried out in dosage units at suitable intervals or in single doses as needed. Usually the method of this invention will be practiced when relief of allergic symptoms is specifically required, however, the method is also usefully carried out as continuous or prophylactic treatment. A particular application is the treatment of various ocular allergies such as vernal keratoconjunctivitis, allergic conjunctivitis, chronic conjunctivitis and giant papillary conjunctivitis by topical administration of these compounds to the eye in a suitable ophthalmic vehicle. Another application is a method of relieving or preventing allergic airway obstruction which comprises administering to an animal a therapeutically effective amount at suitable intervals. It is within the skill of the art to determine by routine experimentation the effective dosage to be administered from the dose range set forth above, taking into consideration such factors as the degree of severity of the allergic condition being treated, and so forth.

The compounds of this invention may be administered in conventional pharmaceutical compositions comprising an appropriate amount of a compound of formula I in association with a pharmaceutical carrier of diluent. The nature of the composition and the pharmaceutical carrier or diluent will, of course, depend upon the intended route of administration, i.e., topically, orally, parenterally or by inhalation. Usually a compound is administered to a mammal in a composition comprising an amount sufficient to produce an inhibition of the symptoms of an allergic response. Whem employed in this manner, the dosage of the composition is such that from 0.5 mg. to 500 mg. of active ingredient are administered at each application. For convenience, equal doses will be administered 1 to 4 times daily with the daily dosage regimen being about 0.5 mg. to about 2000 mg.

For the prophylactic treatment of ocular allergies, the compositions will be in a form suitable for administration by topical application to the eye. Thus, the compositions will comprise a solution or suspension of the active ingredient in a water-based formulation for administration as eye drops, a spray or a suitable solid form for ophthalmic use. For the prophylactic treatment of asthma, the compositions will be in a form suitable for administration by inhalation. Thus, the compositions will comprise a suspension or solution of the active ingredient in water for administration by means of a conventional nebulizer. Alternatively, the compositions will comprise a suspension or solution of the active ingredient in a conventional liquified propellant such as dichlorodifluoromethane or chlorotrifluoroethane to be administered from a pressurized container. The compositions may also comprise the solid active ingredient diluted with a solid diluent, e.g., lactose, for administration from a powder inhalation device. In the above compositions, the amount of carrier or diluent will vary but preferably will be the major proportion of a suspension or solution of the active ingredient. When the diluent is a solid, it may be present in less, equal or greater amounts than the solid active ingredient.

A wide variety of other pharmaceutical forms can be employed. Thus, if a solid carrier is used the preparation can be tableted, placed in a hard gelatin capsule in powder or pellet form, or in the form of a troche or lozenge for oral administration. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampule, or an aqueous or non-aqueous liquid suspension.

Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

The pharmaceutical preparations thus described are made following the conventional techniques of the pharmaceutical chemist involving mixing, granulating and compressing when necessary, or variously mixing and dissolving the ingredients as appropriate to the desired end product.

The following examples illustrate the preparation of compounds of formula I and their incorporation into pharmaceutical compositions and as such are not to be considered as limiting the invention as set forth in the claims appended hereto.

EXAMPLE 1 n-Butyl 2-tert-butoxyacetate

A 500-ml, thick-walled Erlenynmeyer flask equipped with a magnetic stirring bar was cooled to $-78°$ C. (dry iece-acetone bath) and charged with isobutylene (150 ml). Then, n-butyl glycolate (20.0 g, 0.151 mol) and 50 ml of methylene chloride was added along with 1 ml of concentrated sulfuric acid. The cold bath was removed and the mixture stirred for 3 days at room temperature. The reaction was quenched with 50 ml of saturated sodium bicarbonate and the product extracted with ether. The ether layer was dried over sodium sulfate and concentrated. After distillation, the title compound was obtained as a colorless oil: bp 64°-65° C. (0.7 mm).

EXAMPLE 2

2-tert-Butoxyacetic acid

To 100 ml of a 50:50 (v/v) methanol/water solution containing 14.35 g of potassium carbonate, was added n-butyl 2-tert-butoxyacetate (6.50 g, 0.0346 mol). The mixture was heated at reflux for 17 hours and the volatiles removed on a flash evaporator. The remaining solution was cooled to approximately 0° C. and acidified to pH 3–4 with cold 50% aqueous hydrogen chloride. The product was extracted with ether, the ether extract washed with brine and dried over magnesium sulfate, then concentrated in vacuo to give the title compound as a yellow liquid.

EXAMPLE 3

3,5-Bis-N-(2-tert-butoxyacetamido)nitrobenzene 3,5-Diaminonitrobenzene (1.10 g, 0.0072 mol) was placed in a flask with 40 ml of methylene chloride and 1.45 ml of pyridine. The flask was flushed with nitrogen and 2-tert-butoxyacetic acid (2.38 g, 0.0180 mol) was added in 9 ml of methylene chloride. The reaction flask was cooled with an ice water bath and dicyclohexylcarbodiimide (DCC) (3.71 g, 0.18 mol) in approximately 10 ml of methylene chloride was added. The acid solution was then slowly added to the reaction mixture. After approximately 1 hour, the ice bath was removed and the solution stirred for another two hours at room temperature. One ml of water was added to destroy excess DCC. The solution was concentrated under vacuum and diluted with ethyl acetate. Insoluble dicyclohexylurea (DCU) was them removed by filtration. The resulting solution was concentrated in vacuo; the product precipitating spontaneously from the residual solvent. The title compound was further purified by silica gel chromatography using 40% ethyl acetate/hexane.

EXAMPLE 4

3,5-Bis-N-(2-hydroxyacetamido)nitrobenzene

A 25 ml flask was changed with anisole (0.46 g, 0.0043 mol), 3,5-bis-N-(2-tert-butoxyacetamido)nitrobenzene (0.75 g, 0.00197 mol) and 10 ml of a 1:1 mixture of trifluoroacetic acid:chloroform. The reaction mixture was heated at reflux for 17 hours. When cooled to room temperature, a small amount of water was added to the reaction mixture to precipitate the product. The title compound was obtained as a yellow solid after collection by vacuum filtration; mp: 255° C. (decomp.).

EXAMPLE 5

1-Amino-3,5-bis-N-(2-hydroxyacetamido)benzene

A 500-ml Parr hydrogenation bottle was charged with 3,5-bis-N-(2-hydroxyacetamido)nitrobenzene (0.33 g, 0.0012 mol), 10% palladium on carbon (0.33 g) and methanol (250 ml). The bottle was placed on a Parr hydrogenator and pressurized to 30 psi with hydrogen. After 20 hours, the catalyst was removed by filtration through Celite. The solvent was removed in vacuo to yield the title compound as an off-white solid; mp: 135°-137° C.

EXAMPLE 6

5-Acetyl-4-hydroxy-3-[1-[[3,5-bis-N-2-hydroxyacetamidophenyl]amino]ethylidene]2H-pyran-2,6-(3H)-dione A 25 ml flask was charged with 0.14 g of 3,5-diacetyl-4,6-dihydroxy-2H-pyran-2-one (0.14 g, 0.0067 mol), 1-amino-3,5-bis-N-(2-hydroxyacetamido)benzene (0.16 g, 0.0067 mol) and methanol (12 ml). The reaction mixture was heated at reflux for 1.5 hours, then cooled to room temperature. After 15 hours at room temperature, the resulting solid was collected by vacuum filtration. The title compound thus obtained was a tan powder; mp 227°-229° C.; Anal. cal'd: $C_{19}H_{19}N_3O_9$: C 52.65; H 4.42; N 9.70. Found: C 52.44; H 4.65; N 9.50.

EXAMPLE 7

2-(2-Propyl)-1,3-dioxane-5-carboxychloride

A 500-ml flask was charged with 2-(2-propyl)-1,3-dioxane-5-carboxylic acid (10.95 g, 0.63 mol) and 150 ml of ethanol. A solution of potassium hydroxide (3.53 g., 0.63 mol) in 75 ml of ethanol was added dropwise with stirring. After 30 minutes at room temperature, the ethanol was removed in vacuo to yield 13.7 g of the potassium salt as a white solid.

The crude potassium salt (13.64 g, 0.063 mol) was suspended in 100 ml of diethyl ether. Two drops of dimethylformamide were added and the reaction mixture was cooled to 0° C. (ice-water bath). A pressure-equalizing addition funnel was attached and charged with oxalyl chloride (40.8 g, 0.321 mol) which was added dropwise to the potassium salt suspension over a 10 minute period. The reaction mixture was warmed to room temperature and stirred for 2 hours. The potassium chloride was removed by vacuum filtration in a dry box. The filtrate was concentrated in vacuo to yield the title compound as a yellow oil.

EXAMPLE 8

3,5-Bis-N-(2-(2-propyl)-1,3-dioxane-5-carboxamido)nitrobenzene

A 500-ml flask was charged with 3,5-diaminonitrobenzene (2.90 g, 0.019 mol); pyridine (4.50 g, 0.05 mol); 4-dimethylaminopyridine (0.10 g) and dry tetrahydrofuran (150 ml). The reaction mixture was cooled to 0° C. and a pressure-equalizing addition funnel was attached and charged with 2-(2-propyl)-1,3-dioxane-5-carboxylchloride (10.91 g, 0.057 mol) and 20 ml of dry tetrahydrofuran. The acid chloride solution was added dropwise over a 10 minute period. The reaction mixture was then warmed to room temperature and stirred overnight. The solvent was removed in vacuo to yield an orange oil. The oil was taken up in ethyl acetate and washed successively with water, 2.5% hydrochloric acid (to pH 3) and brine. The ethyl acetate layer was dried over magnesium sulfate and concentrated in vacuo to yield a yellow solid which was chromatographed (silica gel; 40% ethyl acetate/hexane to 55% ethyl acetate/hexane) to yield the title compound as an off-white solid.

EXAMPLE 9

3,5-Bis-N-(2-hydroxymethyl-3-hydroxypropionamido)-nitrobenzene

A 25 ml flask was charged with 3,5-Bis-n-(2-propyl)-1,3-dioxane-5-(carboxamido)nitrobenzene (0.38 g, 0.0082 mol), 15 ml of methanol and one drop of concentrated sulfuric acid. The reaction mixture was heated at reflux for 5.5 hours. The reaction mixture was cooled to −20° C. (freezer). After 20 minutes, the title compound was collected by vacuum filtration; mp 202°–205° C., decomp.

EXAMPLE 10

1-Amino-3,5-bis-N-(2-hydroxymethyl-3-hydroxypropionamido)benzene

The title compound was prepared using the method of Example 5. Thus, 3,5-bis-N-(2-hydroxymethyl-3-hydroxypropionamido)nitrobenzene (0.17 g, 0.00048 mmol) was converted to the title compound which was isolated as a rust colored foam.

EXAMPLE 11

5-Acetyl-4-hydroxy-3-[1-[[3,5-bis-N-(2-hydroxymethyl-3-hydroxypropionamidophenyl]amino]ethylidene]-2H-pyran-2,6-(3H)-dione The title compound was prepared using the method of Example 6. Thus, 1-amino-3,5-bis-N-(2-hydroxymethyl-3-hydroxypropionamido)benzene (0.13 g, 0.0004 mol) and 3,5-diacetyl-4,6-dihydroxy-2H-pyran-2-one (0.08 g, 0.0004 mol) were converted to the title compound which was isolated as a white solid; mp: 170°–174° C.; Anal. Calc'd. for $C_{23}H_{27}N_3O_{11}$: C 52.97; H 5.22; N 8.06 Found: C 52.34; H 5.24; N 7.69. Mass spectral analysis: M+ =521.

EXAMPLE 12

Method for Determining Biological Activity

The effect of these compounds on ocular IgE mediated passive anaphylaxis was determined by a method based on the publications of Iso Tadashi, et al. *Ophthalmic Research*, 12: 9–15 (1980) and Harada Minoru, et al, *J. Pharm. Pharmac*, 23: 218 (1971). The results from this assay comparing the stereoisomers of 5-acetyl-4-hydroxy-3-[1-[[3,5-bis-N-(2,3-dihydroxypropionamido)-phenyl]amino]ethylidene]-2H-pyran-2,6-(3H)-dione, here labeled Compound A, with those of the compounds of the present invention where R is —CH$_2$OH (Compound B) and —CH(CH$_2$OH)$_2$ (Compound C) are given in Table I.

TABLE I

| Effects of 2H—pyran-2,6(3H)—diones on IgE Mediated Anaphylaxis | |
|---|---|
| Intravenous Administrations | |
| Compound | I.VED$^{50}$ (ug/kg) |
| Compound A SS isomer | 30 |
| Compound A RR isomer | 300 |
| Compound A Meso isomer | 60 |
| Compound B | 30 |
| Compound C | 30 |

| Topical Administration | | |
|---|---|---|
| Compound$^a$ | Concen. | % Inhibition |
| Compound A SS isomer | 10% | 79% ± 5 |
|  | 5% | 63% ± 8 |
|  | 3% | 40% ± 8 |
| Compound A RR isomer | 3% | 0%$^b$ |
|  | 10% | 16% ± 13 |
| Compound A Meso isomer | 3% | 25% ± 3 |
| Compound C | 5% | 41% ± 4 |
|  | 3% | 31% ± 11 |
|  | 1% | 12% ± 3 |

$^a$Compounds were in the potassium salt form.
$^b$Mediator release was promoted, not inhibited.

What is claimed is:

1. A compound of the formula

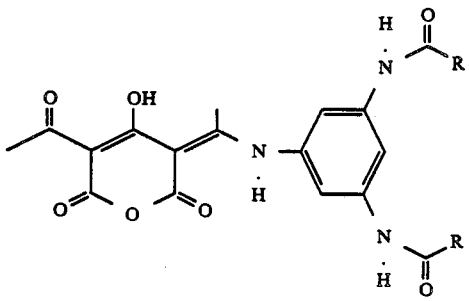

or a pharmaceutically acceptable salt thereof, where R is —(CH$_2$)$_m$OH or —CH((CH$_2$)$_n$CH$_2$OH)$_2$ where m is 1–5 and n is 0–4.

2. A compound of claim 1 where R is —(CH$_2$)$_m$OH and m is 1–5.

3. A compound of claim 2 which is 5-acetyl-4-hydroxy-3-[1-[[3,5-bis-N-2-hydroxyacetamido)phenyl]amino]ethylidene]2H-pyran-2,6-(3H)-dione or a pharmaceutically acceptable salt thereof.

4. A compound of claim 1 where R is —CH((CH$_2$)$_n$CH$_2$OH)$_2$ and n is 0–4.

5. A compound according to claim 4 which is 5-acetyl-4-hydroxy-3-[1-[[3,5-bis-N-(2-hydroxymethyl-3-hydroxypropionamidophenyl]-amino]ethylidene]-2H-pyran-2,6-(3H)-dione or a pharmaceutically acceptable salt thereof.

6. A pharmaceutically acceptable formulation comprising a pharmaceutically acceptable excipient and a therapeutically effective amount of a compound of claim 1.

7. A method for treating ocular allergic diseases, which method comprises administering to the eye a therapeutically effective amount of a compound of claim 1 alone or in admixture with a pharmaceutically acceptable excipient.

* * * * *